United States Patent
Teramoto

[11] Patent Number: 5,967,774
[45] Date of Patent: Oct. 19, 1999

[54] DENTAL ASSIST APPLIANCE FOR ATTACHMENT OF ORTHODONTIC WIRE AND ORTHODONTIC APPLIANCE USING IT

[76] Inventor: Nobuhisa Teramoto, 396 Hatagawa, Kainan-shi, Wakayama, Japan

[21] Appl. No.: 09/018,945

[22] Filed: Feb. 5, 1998

[30] Foreign Application Priority Data

Feb. 5, 1997 [JP] Japan .................................. 9-22650

[51] Int. Cl.[6] .................................................. A61C 3/00
[52] U.S. Cl. ................................................ 433/22; 433/18
[58] Field of Search .............................. 433/5, 7, 18, 19, 433/21, 22, 24

[56] References Cited

U.S. PATENT DOCUMENTS

| | | | |
|---|---|---|---|
| 783,609 | 2/1905 | Canning | 433/21 |
| 2,580,042 | 12/1951 | Paus | 433/21 |
| 3,293,747 | 12/1966 | Denholtz | 433/21 |
| 4,202,100 | 5/1980 | Forster | 433/7 |
| 4,255,139 | 3/1981 | Ladanyi | 435/21 |
| 4,439,148 | 3/1984 | Haas | 433/7 X |
| 4,723,910 | 2/1988 | Keller | 433/7 |
| 5,011,404 | 4/1991 | Losi | 433/21 X |
| 5,064,370 | 11/1991 | Jones | 433/18 X |
| 5,299,935 | 4/1994 | Lokar | 433/18 |
| 5,711,667 | 1/1998 | Vogt | 433/21 X |

OTHER PUBLICATIONS

The Base Technique of Correction for Dentist In Practice (Author: Osamu Aoshima)—Dental Diamond Co., Ltd. Mar. 31, 1990.
Dental Correction Technique (Author: Tetsuo Iisuka) Medicine & Dental Medine Co., Ltd. Apr. 5, 1976.
Limited Correction Treatment Atlas for Adults Japan Dental Publish Co., Ltd. Feb. 10, 1984.

Primary Examiner—Nicholas D. Lucchesi
Attorney, Agent, or Firm—Edwin E. Greigg; Ronald E. Greigg

[57] ABSTRACT

A dental assist appliance for attachment of an orthodontic wire for achieving an effective correction of irregularities of the teeth or of improper dental arch for a short time. The dental assist appliance includes a base shaft member and an elastic member having one end fixed to said base shaft member and the other end formed as a sliding portion slidable along said base shaft member. Further, an orthodontic appliance using the dental assist appliance includes two dental assist appliances each having a sliding portion; and a dental orthodontic wire interposed between the sliding portions of the two dental assist appliances.

14 Claims, 7 Drawing Sheets

Fig. 9

DENTAL ASSIST APPLIANCE FOR ATTACHMENT OF ORTHODONTIC WIRE AND ORTHODONTIC APPLIANCE USING IT

BACKGROUND OF THE INVENTION

1. Field of the Invention

The present invention relates to a dental assist appliance for guiding movement of an orthodontic wire for correcting malocclusion (irregularities of teeth or an improper dental arch) and to an orthodontic appliance using it.

2. Description of the Prior Art

In general, for correcting irregularities of the teeth or an improper dental arch of anterior cross-bite (mandibular protrusion), a method in which a force is exerted on front teeth of the upper jaw so that the front teeth of the upper jaw can be moved toward the front of the front teeth of the lower jaw is typically used. Some typical examples of the method are given below.

An orthodontic wire having a diameter of about 0.5 mm, which is called an accessory spring, is brought into contact with a neck portion (a boundary between a tooth and a gum) of each tooth to be corrected at the back side (at the tongue side) so that the each tooth can be pushed forwards by the resilient force, to correct the irregularities or improper dental arch of the front teeth (Lingual Arch Method).

An elastic orthodontic wire, after fit-in from the lip side of the teeth with spaced therefrom, is fixed at its opposite ends to both molar teeth of the upper jaw with fittings. Then, the orthodontic wire is deflected to the surface of each of the front teeth to be corrected at the lip side of the teeth and is ligatured thereto. The ligatured front teeth are each retracted toward the tongue side by the resilience of the elastic orthodontic wire, to correct the irregularities or improper dental arch of the front teeth (Utility Arch Method).

A detachable inclined plane, formed in accordance with irregularities of the teeth or improper dental arch, is bitten, and the resulting force is exerted on the front teeth to be corrected, to correct the irregularities or improper dental arch of the front teeth (Inclined Plane Method).

By the aid of resilience of a pair of rubbers mounted on a headgear, a pad at one's chin is retracted backwards, to suppress the growth of the chin, to correct the irregularities or improper dental arch of the teeth (Chin Cap Method).

Figure 6:
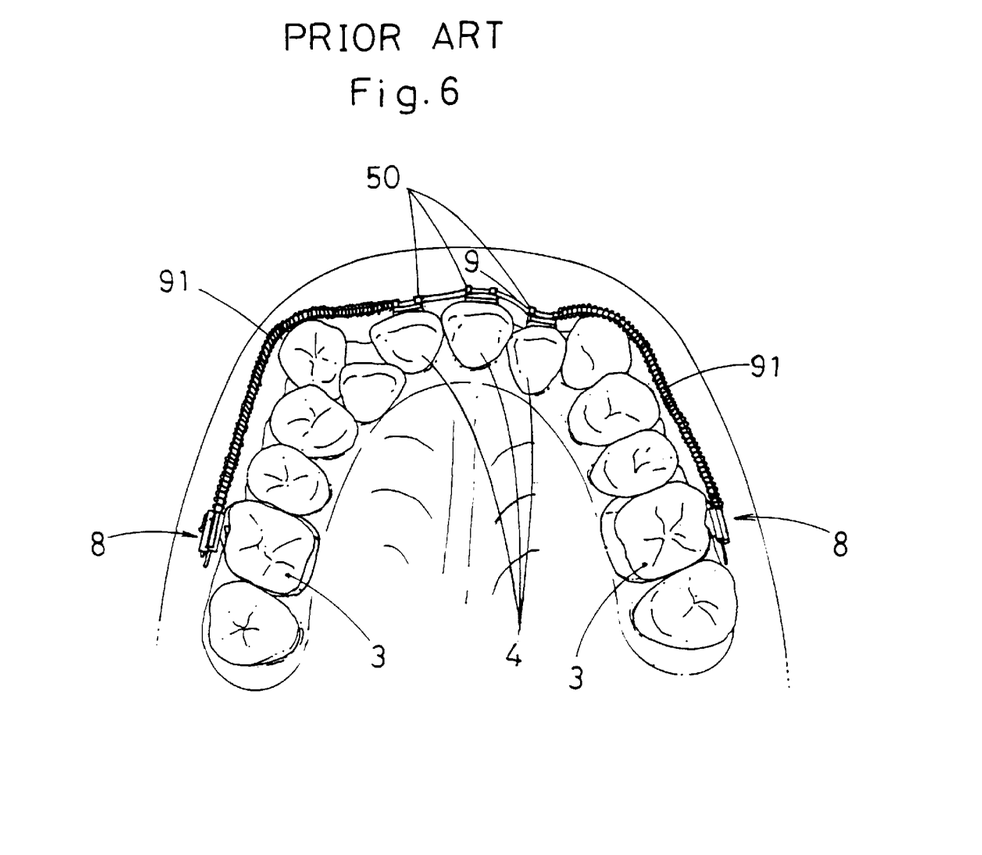
FIG. 6 is a showing of a portion of the upper jaw to which a conventional type orthodontic appliance is fitted as viewed from below.

As shown in FIG. 6, an orthodontic wire 9, which is slidably fitted at its opposite ends to fixings 8, 8 fixed to molars 3, 3, is so secured as to extend along teeth at the lip side of the upper jaw.

The orthodontic wire 9 is ligatured (fixed) to brackets 50 bonded to front teeth 4 to be corrected. Coiled springs 91, 91 are fitted around portions of the orthodontic wire 9 extending between the fixings 8 for the orthodontic wire 9 and the brackets 50. The coiled springs 91, 91 at right and left sides, each of which is restricted at one end thereof by the fixing 8, allow the orthodontic wire 9 and the front teeth 4 ligatured thereto to be pushed forwards, to correct the irregularities or improper dental arch of the teeth.

However, the conventional methods mentioned above have the following disadvantages:

The method has the disadvantage that as the tip ends of the teeth are shifted forwards, an angle at which the accessory spring fitted to the teeth at the tongue side contacts with the surfaces of the teeth decreases, and as a result, the elastic aiding wire slips on the tooth surface at the tongue side to reduce or lose the effect.

The method using the deflection of the orthodontic wire has the disadvantage that the force exerting on the front teeth is weaken soon. For all that, if the force exerting on the front teeth is increased by increasing the degree of deflection of the orthodontic wire or by replacing it with a stronger resilient one, that arises a possible problem that the wire may contact with the lip or gum to cause an ulcer, or an excessive force may be exerted on the teeth to cause pain.

The method has the disadvantage that the inclined plane must be bitten with a weak force for long hours to take effect.

The method does not work quickly and may possibly cause a jaw-joint disorder during a long time, depending on a magnitude of force.

The method has the disadvantage that a portion of the pushing force from the coiled spring does not work in the direction for the front teeth to be shifted forwards, but acts in the direction for the front teeth to be retracted inside (median), with the result that satisfactory orthodontics cannot be achieved or it takes long tome till the completion of the orthodontics.

Further, these five methods above have the common disadvantage that the medical appliance must be attached for long hours to take effect.

SUMMARY OF THE INVENTION

To eliminate or minimize the disadvantages above, the present invention has been proposed. It is the object of the invention to provide an orthodontic appliance capable of achieving effective orthodontics of malocclusion for a short time, as compared with the known ones.

To accomplish the above described object, the present invention is directed to a novel dental assist appliance for attachment of an orthodontic wire comprising a base shaft member and an elastic member having one end fixed to the base shaft member and the other end formed as a sliding portion slidable along the base shaft member.

The dental assist appliance for attachment of an orthodontic wire according to the present invention may comprise holding means for holding the sliding portion in a specified position against a biasing force of the elastic member.

The dental assist appliance for attachment of an orthodontic wire according to the present invention may comprise position limiting means for preventing said sliding portion from sliding beyond a preset position.

Preferably, the dental assist appliance for attachment of an orthodontic wire according to the present invention is provided with a retaining member.

Further, the present invention is directed to a novel orthodontic appliance comprising two dental assist appliances each having a sliding portion; and an orthodontic wire interposed between the sliding portions of the two dental assist appliances.

BRIEF DESCRIPTION OF THE DRAWINGS

The orthodontic appliance according to the present invention will now be described with reference to the accompanying drawings showing the embodiments wherein.

DETAILED DESCRIPTION OF THE PREFERRED EMBODIMENT

Referring now to the accompanying drawing figures, examples of the preferred embodiment of the orthodontic appliance of the present invention are described below. It is to be understood, however, that the scope of the invention is by no means limited to the illustrated embodiments.

Figure 1:
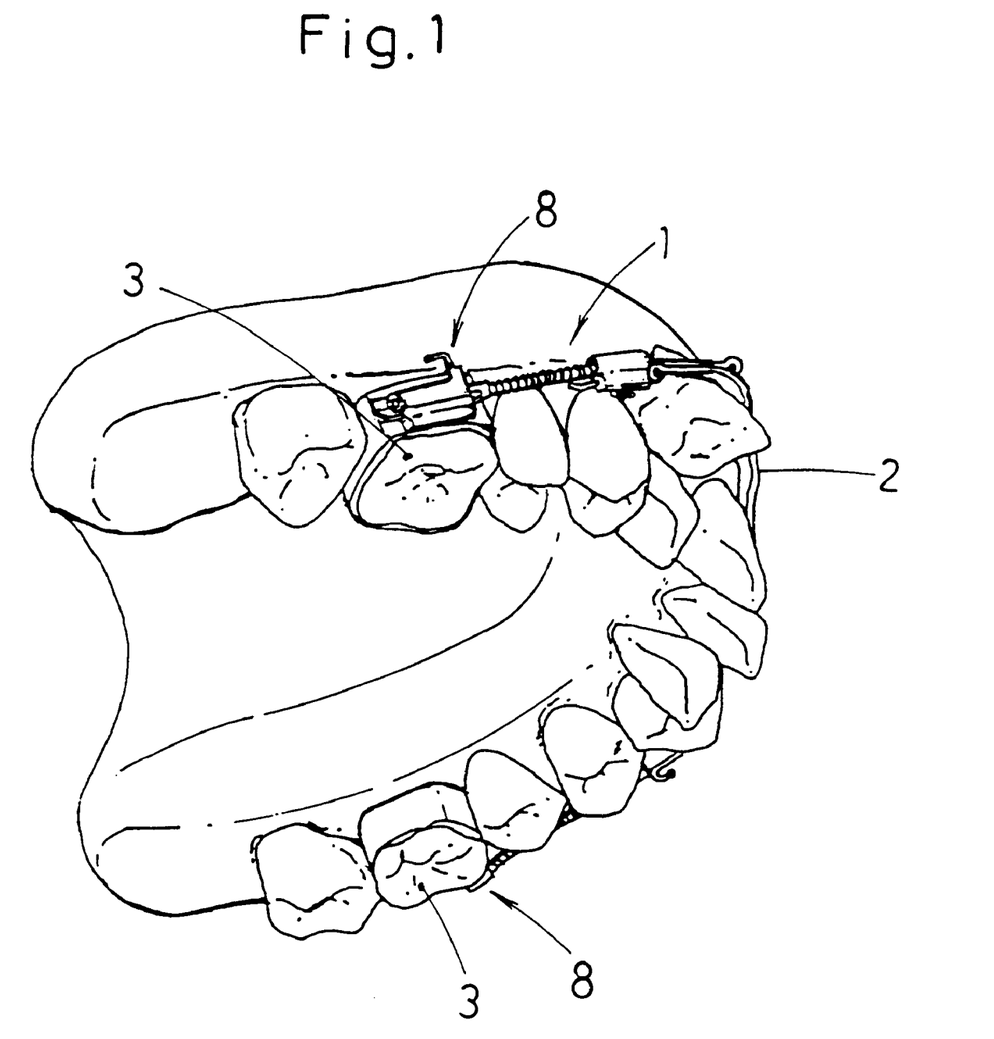
FIG. 1 is a perspective view of a portion of the upper jaw to which the orthodontic appliance of the invention is fitted.
Figure 2A:
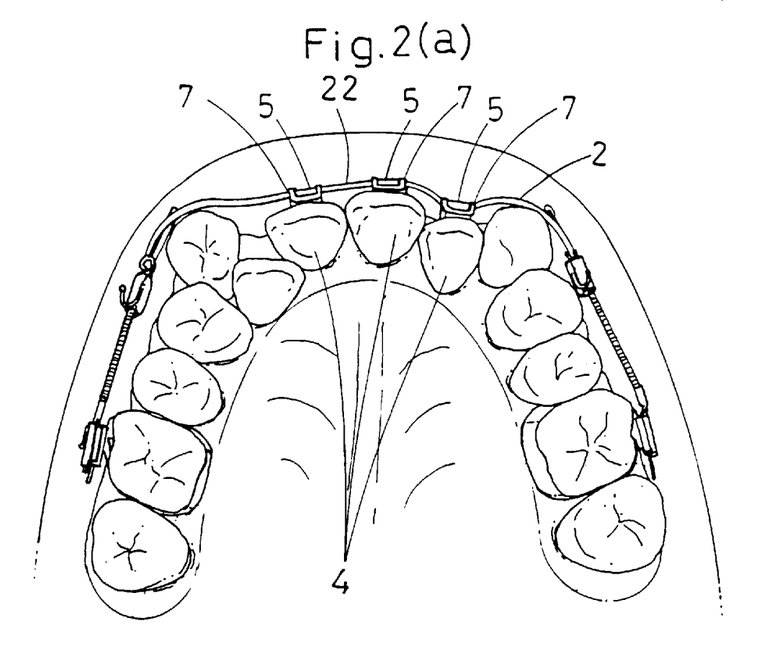
FIG. 2a and 2b are a showing of the same viewed from below.
Figure 2B:
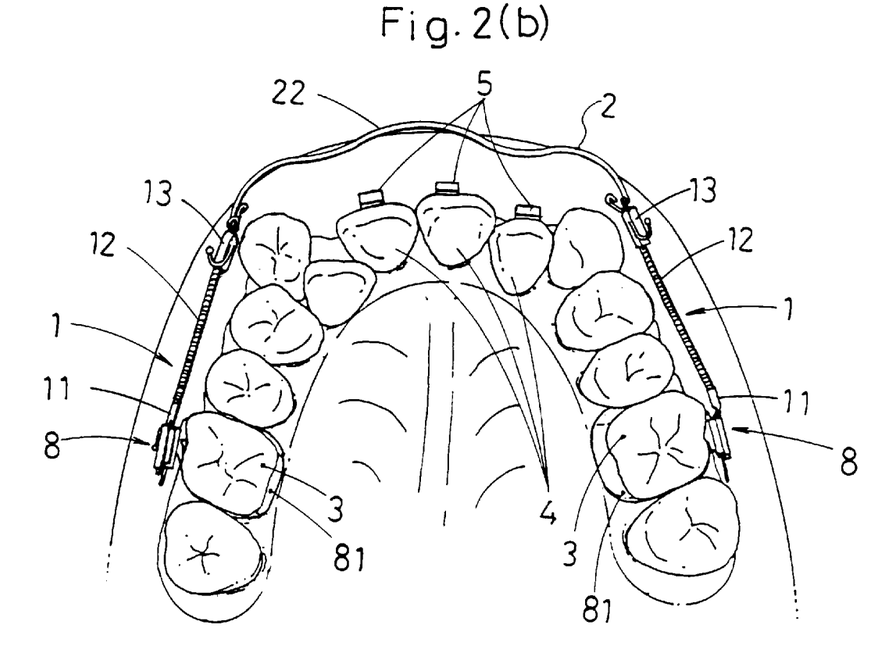
Figure 3A:
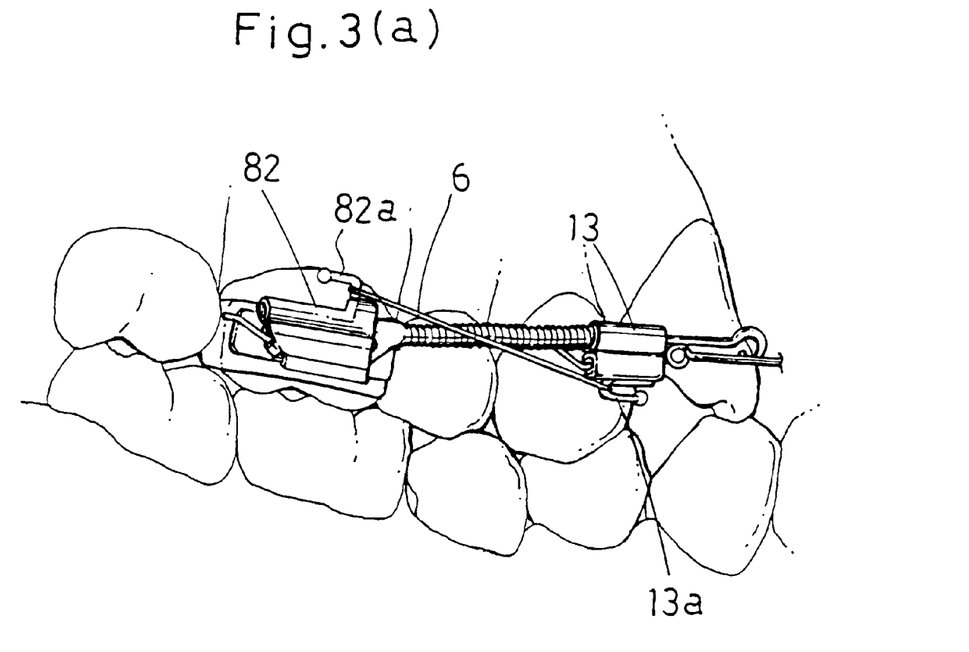
FIG. 3a and 3b are a partially enlarged view of the same orthodontic appliance.
Figure 3B:
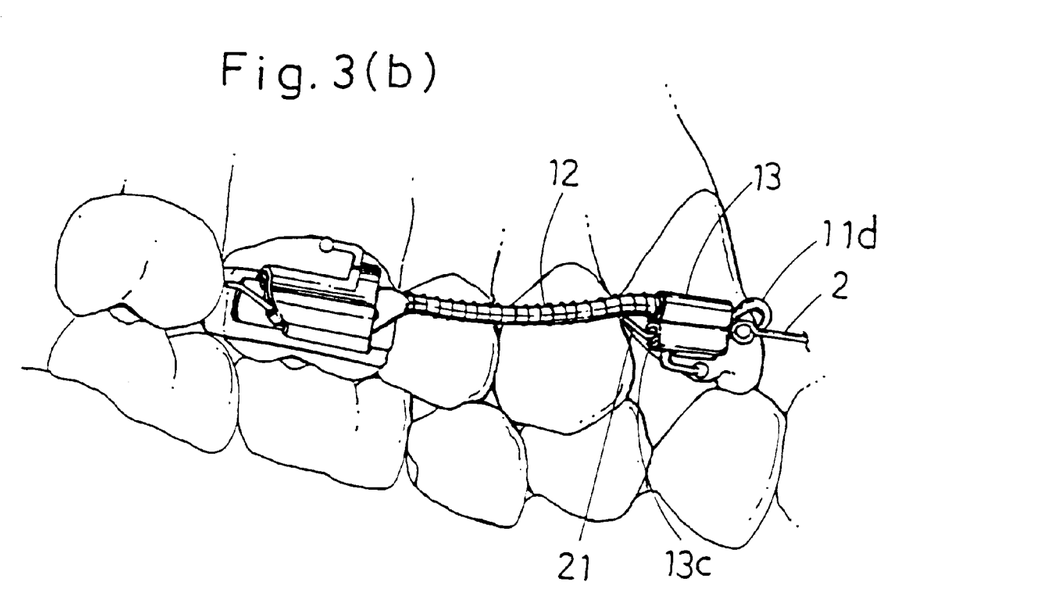

FIG. 1 is a perspective view of a portion of the upper jaw to which the orthodontic appliance of the present invention is fitted; FIG. 2a and 2b are a showing of the same viewed from below; FIG. 3 a and 3b are partially enlarged view of the same orthodontic appliance; and FIG. 4a and 4b are partial illustrations of a guide wire.

The orthodontic appliance shown in FIG. 1 comprises guide wires 1, 1 fixed to right and left molars 3, 3 by fixings 8, 8; and an orthodontic wire 2 which is guided at the opposite ends by the guide wires 1, 1 to be movable in the back-and-forth direction. Almost all the components are made of a metallic substance, harmless to humans, such as stainless steel or cobalt chrome.

Figure 4A:
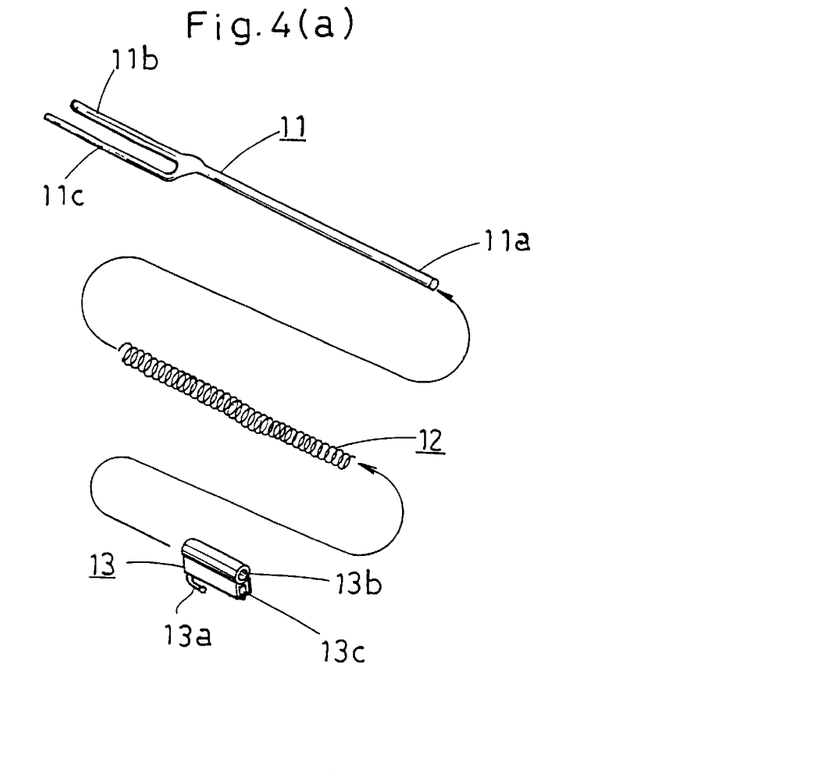
FIG. 4a and 4b are a perspective view of a guide wire and fixings of the orthodontic appliance of FIG. 1.
Figure 4B:
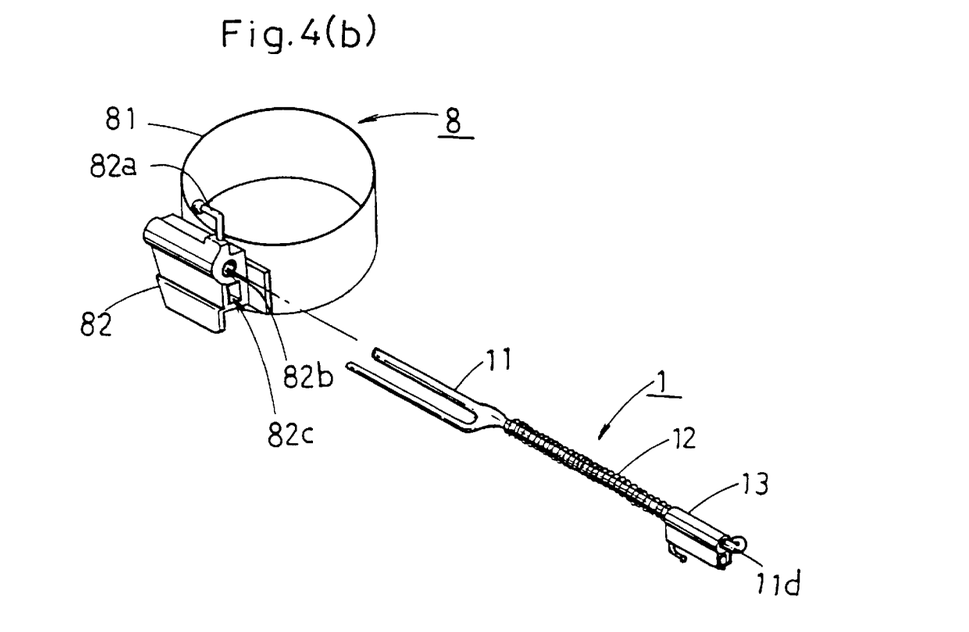

Each of the guide wire 1 comprises, as shown in FIG. 4 (a)(b), a Y-shaped wire 11 having a fork end, a coiled spring 12 made of nickel titanium, and a tube 13 having two through holes. The Y-shaped wire 11 is formed by a thin wire 11c having a diameter of about 0.4 mm and a length of about 1 cm being brazed to an end portion of the wire, having a diameter of about 0.8 mm and a length of about 4 cm, in the vicinity of the distal end 11b. The tube 13 has a circular hole 13b at a top portion thereof; a rectangular hole 13c at a portion thereunder, both extending in parallel in a lengthwise direction; and a hook 13a at a bottom portion thereof.

The guide wire 1 is assembled in the following way. A front end portion 11a of the Y-shaped wire 11 is inserted into the coiled spring 12 and then is inserted into the circular hole 13b at the top portion of the tube 13, with the coiled spring 12 being pressed by the tube 13. Then, the front end portion 11a is bent at its tip to form a loop 11d, so as to prevent the tube 13 from being fallen out. The tube 13 is fitted to the Y-shaped wire 11 in a slidable manner.

On the other hand, each of the fittings 8 comprises a band 81 to be fitted onto a tooth and a tube 82 brazed to the band 81. In the tube 82, a circular hole 82b and a rectangular hole 82c are bored, and a hook 82a is provided at the top of the tube 82. The holes bored in the tubes 13 and 82 may be formed into either of the circular hole and rectangular hole.

In the terminology used herein, the guide wire 1 corresponds to the dental assist appliance; the orthodontic wire 2 corresponds to the dental orthodontic wire; the Y-shaped wire 11 corresponds to a base shaft member; the loop 11d corresponds to position limiting means; the coiled spring 12 corresponds to an elastic member; and the tube 13 corresponds to a sliding portion.

As shown in FIG. 4(b), the guide wire 1 is fitted to the fitting 8, with the distal end 11b and the wire 11c of the Y-shaped wire 11 inserted in the circular hole 82b and the rectangular hole 82c, respectively. Of course, without having to provide the wire 11c, the guide wire 1 may be fitted to the fitting 8 by the distal end portion 11b of the Y-shaped wire 11 being inserted into the hole 82b and bonded thereto with adhesive. In this modification, the hole 82b should be formed into a rectangular or ellipse shape in section, for the purpose of preventing the relative rotation therebetween. In the illustrated embodiment, since the guide wire 1 is pressed and biased against the fitting 8, the guide wire 1 need not be necessarily fixed to the fitting 8.

Next, description on the fitting way and the use of the orthodontic appliance is given below with reference to FIGS. 2 and 3.

Three front teeth 4 shown in FIGS. 2(a)(b) are those having irregularities to be corrected.

One of the fittings 8, having a band 81 enough large to fit onto the molar 3, is selected and is pressed onto its related molar 3 to be fixed. The distal end portion 11b and wire 11c of the guide wire 1 are inserted into the circular hole 82b and rectangular hole 82c of the tube 82 of the fitting 8 fixed to the molar 3, respectively, and fitted thereto (See FIG. 2b).

The other of the fittings 8 is fitted to its related molar 3 in the same manner.

The brackets 5 are adhesive bonded to the lip-side surfaces of the three front teeth 4 to be corrected, respectively (See FIG. 2b).

The orthodontic wire 2 is bent to suit for the positions of the front teeth 4 (See FIG. 2b).

After the orthodontic wire 2 is looped at its portions close to the distal ends 21, the distal ends 21 are passed through the rectangular holes 13c of the tubes 13. One of the distal ends 21, extending outwards from the rectangular hole 13c, is slightly bent so that it can be secured in position without slipping off. However, the distal end may be simply inserted in the rectangular hole, because, in the condition of the orthodontic wire 2 being ligatured to the teeth 4, the distal end 21 of the orthodontic wire 2 is pressed against the tube 13 and thus hardly slip therefrom. Additionally, the distal end 21 inserted in the rectangular hole 13c may, of course, be riveted from outside or be adhesive bonded in the hole, to thereby be bonded together (See FIG. 3b).

The other distal end 21 at the opposite side is also loosely inserted in or bonded in its related rectangular hole 13c of the tube 13 in the same manner. In this state, the orthodontic wire 2 is biased to the lip side by the coiled spring 12, so that the orthodontic wire is spaced apart from the teeth 4 at given intervals (See FIG. 2b and FIG. 3b).

A center portion 22 of the orthodontic wire 2 confronting the front teeth 4 is pushed to the tongue side to bring the tube 13 close to the tube 82, and a rubber band 6 is hung on the hook 13a and the hook 82a at one side, to keep the distance between the tube 13 and the tube 82 at the shortest distance. The hook 13a, the hook 82a and the rubber band 6 correspond to the holding means according to the invention (See FIG. 2a and FIG. 3a).

Similarly, another rubber band 6 is hooked on the tube 13 and the tube 82 at the opposite side, to keep the distance therebetween at the shortest distance. The center portion 22 of the orthodontic wire 2 is then pressed against the brackets 5 at the front teeth 4 (See FIG. 2a and FIG. 3a).

The center portion 22 of the orthodontic wire 2 is fitted to the brackets 5 at the front teeth 4 by use of small rubber bands 7 or ligature wires (See FIG. 2a).

After completion of the fitting, the rubber bands 6 are cut to allow the orthodontic wire 2 to be biased toward the lip by the resilience of the coiled spring 12 and in turn allow the front teeth 4 fitted to the center portion 22 of the orthodontic wire 2 to be retracted to the lip side.

In the event that the hook 13a comes to contact with the lip to form an obstacle, the hook may be filed away with a file or the like.

The front teeth 4 under orthodontics are gradually shifted to the lip side through the action of the orthodontic wire 2, but the tube 13 is prevented by the loop 11d from sliding beyond the loop 11d formed at the front end portion 11a of the Y-shaped wire 11. In other words, the orthodontic wire 2 cannot move forwards across the position shown in FIG. 3b set by the above described operations and, with the result that any further force is not exerted on the front teeth 4. Hence, even if some reason prevents a patient from visiting a dentist to have his/her teeth cured for a long time, the teeth are prevented from shifting too much to the lip side.

Figure 7:
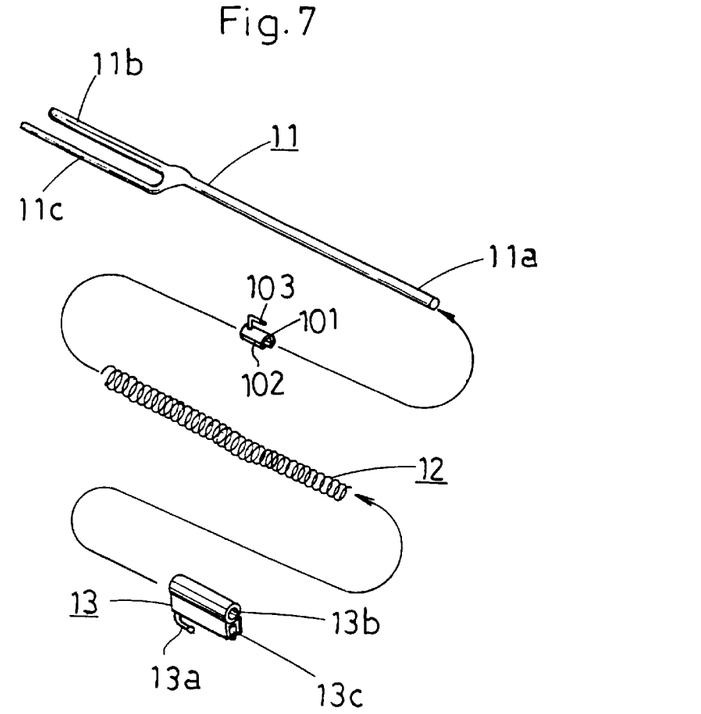
FIG. 7 is an exploded perspective view of a dental assist appliance of another embodiment.
Figure 8:
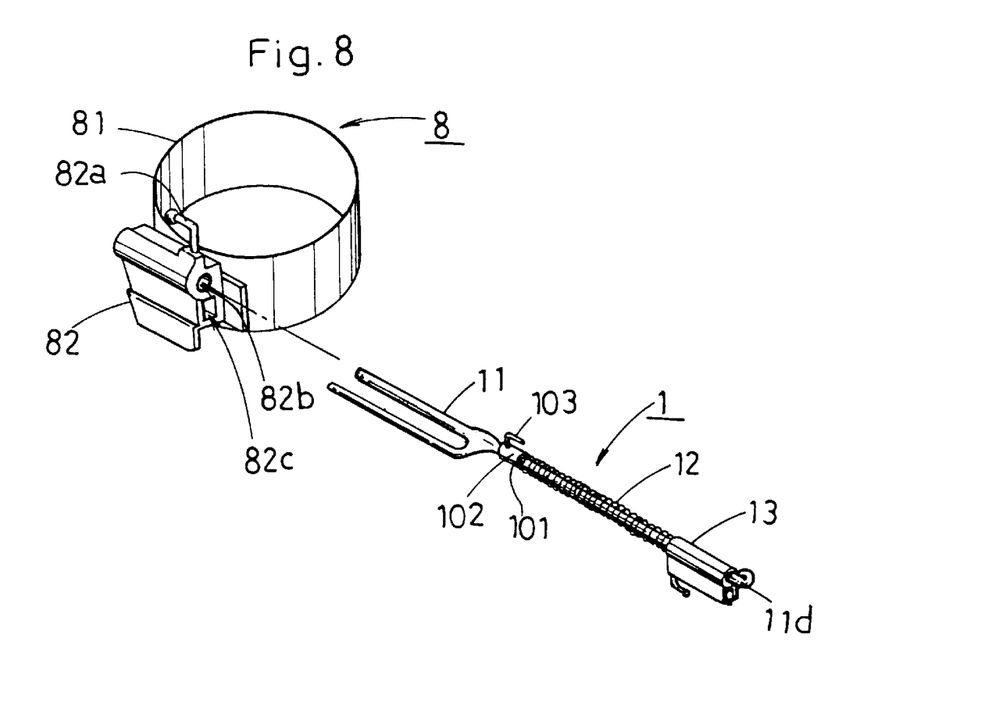
FIG. 8 is a perspective view of the dental assist appliance and the fixings shown in FIG. 7.
Figure 9:
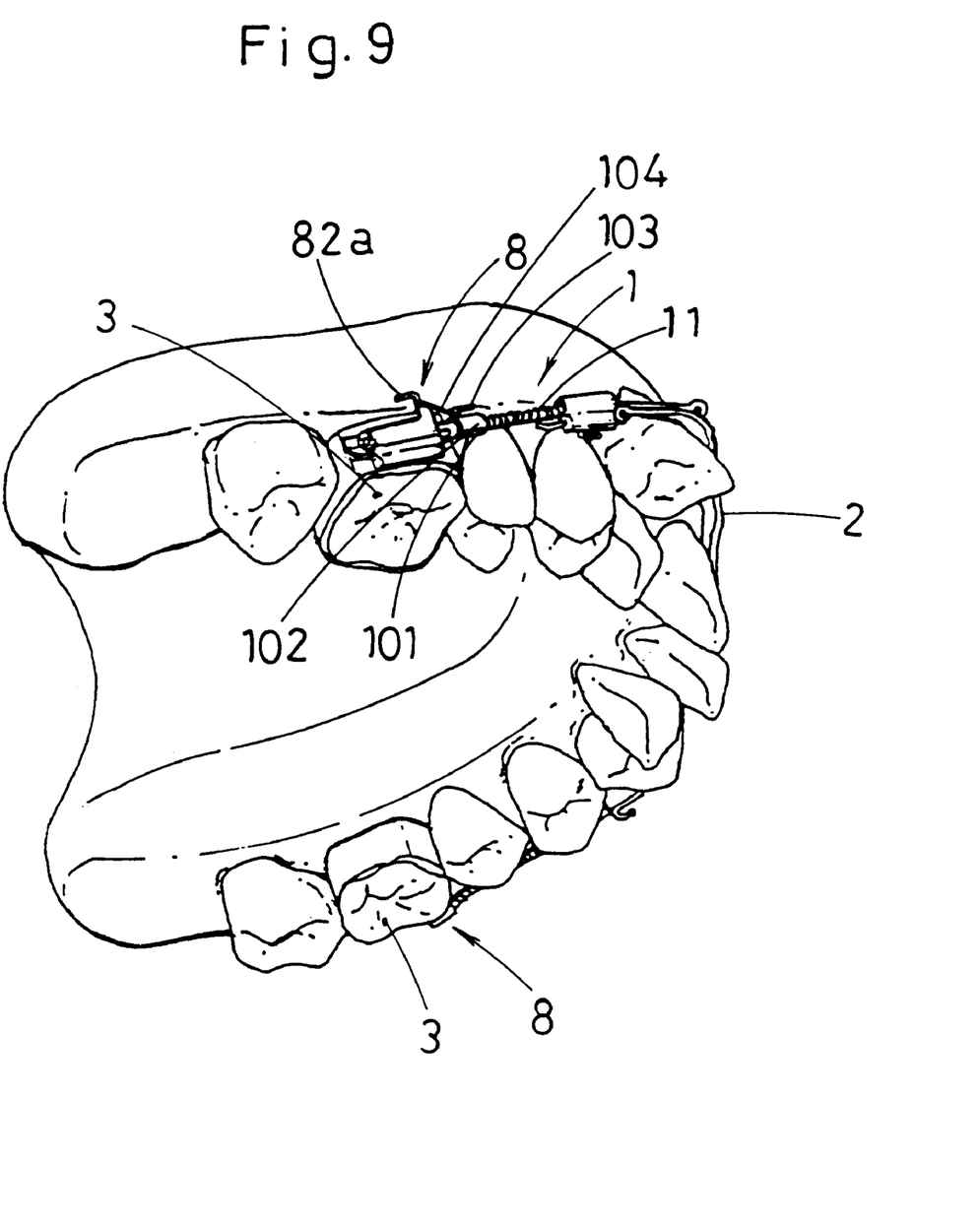
FIG. 9 is a perspective view showing the state of use of the dental assist appliance shown in FIG. 7.

Shown in FIGS. 7 to 9 is a modification by adding a retaining member 101 to construction of the above-mentioned embodiment (See FIG. 4(a),(b)).

The retaining member 101 comprises a cylindrical portion 102 which is notched at one part thereof in the lengthwise direction so as to be brazed to or detachably engaged with the Y-shaped wire 11; and a hook portion 103 formed on the cylindrical portion 102.

In use, as shown in FIGS. 8 and 9, the cylindrical portion 102 is fitted to the Y-shaped wire 11, and then the hook portion 103 and the hook 82a of the fitting 8 are fastened together by a wire 104, whereby it is ensured that the wire guide 1 (the dental assist appliance) can be prevented from being disengaged from the fitting 8 during the use. The wire 104 may, of course, be fastened directly to the wire guide 1, rather than to the hook 82a. The remaining of the modification is identical in structure, operation and effect to the embodiment illustrated in the other Figures, so the same reference numerals are affixed to the same elements in each of several Figures, to avoid repetition of the description thereon.

The orthodontic appliance according to the present invention is not limited to the above-illustrated embodiments. For example, the rubber band 6 as the holding means may be replaced with a rod of a given length having a hook at each end. Also, the end portion of the coiled spring (the elastic member) may be fitted directly to the distal end of the dental orthodontic wire.

Figure 5:
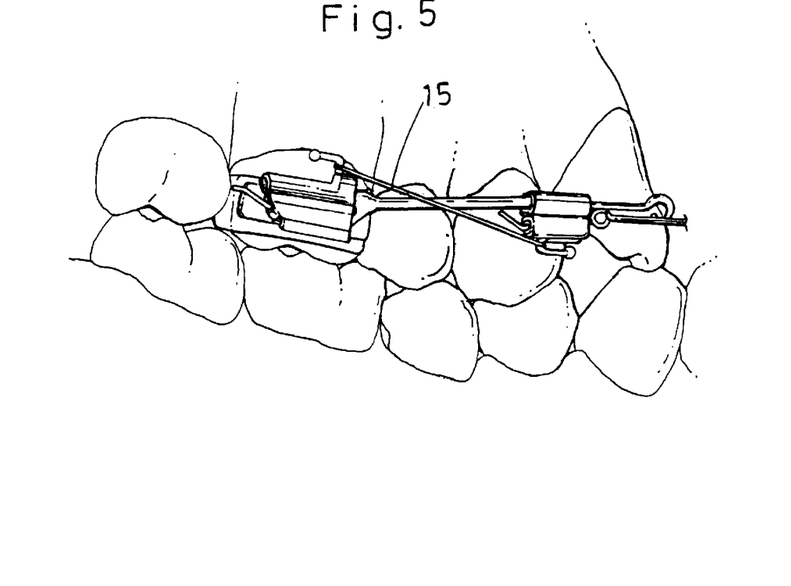
FIG. 5 is an enlarged view of a portion of the upper jaw to which an orthodontic appliance of another embodiment is fitted.

Further, the above-mentioned orthodontic appliance may be applied for correction of an excessively protruded front teeth of the lower jaw (anterior cross-bite) or an excessively protruded front teeth of the upper jaw (buckteeth) by pressing them to the tongue side. In this case, the above-described coiled spring 12 is replaced to the one that biases the orthodontic wire in the retracting direction. Alternatively, the coiled spring may be removed, but instead the rubber band 15 may be used as the elastic member for biasing the orthodontic wire in the retracting direction, as shown in FIG. 5. In this case, the orthodontic wire is pressed against the teeth to be corrected, so that no holding means is necessary.

What is claimed is:

1. An orthodontic appliance comprising at least one dental assist appliance to which one end of an orthodontic wire is attached and one end of said dental assist appliance is attached to a fitting (8) which is in turn adapted to be secured to a tooth, said dental assist appliance comprises a base shaft member (11) including a free end (11a) and a forked end (11b, 11c) which is secured to said fitting (8), an elastic member (12) is slidably fitted onto said free end of said base shaft member with said elastic member extending to said forked end of said base shaft member, a slide member (13) which is slidably secured onto said free end of said base shaft member, with said slide member in touch with said elastic member, and said slide member is prevented from sliding from said free end of said base shaft member, said forked end of said base shaft member is secured to said fitting (8) and one end of said orthodontic wire is secured to said slide member, and said orthodontic wire is adapted to be secured to the teeth to assist in correcting the teeth.

2. An orthodontic appliance according to claim 1, further comprising holding means for holding said base shaft member in a specified position on said free end of said slide member against a biasing force of said elastic member.

3. An orthodontic appliance according to claim 1, further comprising position limiting means formed by bending said free end of said base shaft member at a certain portion of said base shaft member for preventing said slide member from sliding beyond a preset position.

4. An orthodontic appliance according to claim 1, wherein said base shaft member is provided with a retaining member juxtaposed said forked end.

5. An orthodontic appliance for correcting misaligned teeth, which comprises:

first and second base shaft members, each sharing a Y-shaped first end including first and second wire portions and a cylindrical wire portion with a straight second end;

first and second elastic members slidably fitted onto said second end of said first and second base shaft members, respectively;

first and second sliding members slidably fitted onto said second end of said first and second base shaft members, respectively, with said second end passing through said sliding members and provided with means for preventing removal of said second end of said first and second base shaft members from said first and second sliding members, respectively;

a dental orthodontic wire interposed between said first and second sliding members with ends of said orthodontic wire secured to said first and second sliding members; and first and second tooth engaging members secured to said first end of said first and second base shaft members, respectively.

6. An orthodontic appliance as set forth in claim 5, in which each of said first and second sliding members include parallel passages through a length thereof.

7. An orthodontic appliance as set forth in claim 6, in which one of said parallel passages is cylindrical and another one is non-cylindrical.

8. An orthodontic appliance as set forth in claim 6, wherein said straight second end of said first and second base shaft members fits into one of said parallel passages and one end of said orthodontic wire fits into another parallel passage of each of said sliding members.

9. An orthodontic appliance as set forth in claim 5, in which each of said first and second tooth engaging members include a band (81) that fits onto a tooth;

said band is secured to a supporting body portion (82), and said supporting body portion includes parallel passages along a length thereof.

10. An orthodontic appliance as set forth in claim 9, in which one of said parallel passages in said supporting body portion of said tooth engaging members is cylindrical, and another parallel passage is non-cylindrical.

11. An orthodontic appliance as set forth in claim 9, wherein the first end portion of said Y-shaped end of said first and second base shaft members is cylindrical and fits into said cylindrical parallel passage of said body portion of said tooth engaging members and said second end portion of said Y-shaped end is non-cylindrical and fits into said non-cylindrical passage of said body portion of said tooth engaging members.

12. An orthodontic appliance as set forth in claim 11, wherein each of said first and second elastic members are slidably fitted onto said second end of each of said first and second Y-shaped members and are positioned between each of said tooth engaging members and each of said first and second sliding members, respectively.

13. An orthodontic appliance as set forth in claim 5, in which each of said first and second tooth engaging members and each of said first and second elastic slide members include a hook thereon with each of said hooks facing away from each other.

14. An orthodontic appliance as set forth in claim 13, which includes an elastic band (15) for connecting to each of said hooks.

\* \* \* \* \*